United States Patent [19]

Bahr et al.

[11] Patent Number: 4,796,184
[45] Date of Patent: Jan. 3, 1989

[54] AUTOMATIC BLOOD PRESSURE MEASURING DEVICE AND METHOD

[75] Inventors: Dennis E. Bahr, Middletown; Kenneth R. Clark, Cottage Grove; Kendall E. Post, Madison, all of Wis.

[73] Assignee: Cas Medical Systems, Inc., Branford, Conn.

[21] Appl. No.: 892,848

[22] Filed: Aug. 1, 1986

[51] Int. Cl.⁴ .............................................. A61B 5/02
[52] U.S. Cl. ................. 364/413.03; 128/681; 128/682
[58] Field of Search ................. 364/417, 416; 128/680, 128/681, 682, 685, 686

[56] References Cited

U.S. PATENT DOCUMENTS

| | | | |
|---|---|---|---|
| 4,262,675 | 4/1981 | Kubo et al. | 128/680 |
| 4,349,034 | 9/1982 | Ramsey, III | 128/681 |
| 4,360,029 | 11/1982 | Ramsey, III | 128/681 |
| 4,427,013 | 1/1984 | Nunn et al. | 128/681 |
| 4,461,266 | 7/1984 | Hood et al. | 128/681 |
| 4,543,962 | 10/1985 | Medero et al. | 128/682 |
| 4,546,775 | 10/1985 | Medero | 128/681 X |
| 4,564,020 | 1/1986 | Link | 128/677 |
| 4,625,277 | 11/1986 | Pearce et al. | 364/416 |
| 4,638,810 | 1/1987 | Ramsey, III et al. | 128/681 |
| 4,646,754 | 3/1987 | Seale | 128/677 X |
| 4,664,126 | 5/1987 | Link | 128/681 |
| 4,669,485 | 6/1987 | Russell | 128/681 X |

Primary Examiner—Jerry Smith
Assistant Examiner—Charles B. Meyer
Attorney, Agent, or Firm—William W. Jones

[57] ABSTRACT

The device measures blood pressure automatically using the oscillometric technique. The device includes a pressure cuff which is automatically inflated to an initial pressure which is calculated to be above the subject's systolic pressure. The cuff is then deflated stepwise in preset pressure increments while cuff pressure oscillations are sensed at each cuff pressure level and stored in a computer incorporated into the device. Cuff deflation is continued until the cuff pressure is below the subject's diastolic pressure whereupon the cuff is automatically deflated. The computer then fits a calculated parabolic curve onto the greatest cuff pressure oscillation and onto a lesser oscillation on each side of the greatest oscillation. From the thusly derived curve, the computer determines the mean blood pressure, and the systolic and diastolic blood pressures.

17 Claims, 6 Drawing Sheets

AUTOMATIC BLOOD PRESSURE MEASURING DEVICE AND METHOD

This invention relates to an improved device for automatically measuring mean, systolic and diastolic blood pressures by the oscillometric technique. More particularly, the device of this invention takes actual cuff oscillations resulting from blood vessel wall movement and fits a parabolic curve onto selected ones of these cuff oscillations and then uses the resultant curve to calculate the statistically true mean, systolic, and diastolic blood pressures.

The measurement of systolic, diastolic and mean blood pressure values by measuring cuff pressure oscillations caused by blood vessel pulses during stepwise deflation of the cuff is a known technique. Methodology and apparatus for automatically performing this general technique are disclosd in U.S. Pat. No. 4,349,034 granted Sept. 14, 1982 to M. Ramsey and U.S. Pat. No. 4,360,029 granted Nov. 23, 1982 to M. Ramsey. These patent disclosures relate to a technique which uses a computer controlled device to inflate a pressure cuff, stepwise deflate the cuff, measure and store cuff pressure oscillations occurring at each deflation plateau, and determine which cuff pressure oscillation was the largest. The device then identifies the cuff pressure at which the largest oscillation took place as the mean blood pressure. Provisions are made for rejecting artifact cuff pressure oscillations which can result from subject movement, accidental contact with the pressure cuff, and the like.

A device similar to that disclosed in the aforesaid patents is described in an article authored by Joseph Erlanger, M.D., published in *The Johns Hopkins Hospital Reports* Vol. XII by the Johns Hopkins Press (1904). In the Erlanger device, the cuff was automatically inflated to an initial pressure above mean, and then stepwise deflated to a pressure below mean. Cuff pressure oscillations were sensed and traced onto a rotating drum sheet by a floating pen. Artifact oscillations will be apparent upon viewing the trace.

It will be noted that in both the Erlanger and Ramsey devices, the pressure identified as mean blood pressure is one of the stepwise cuff pressures. The drops in pressure will be in 5 to 10 mmHg per step, according to the prior art.

If one were to connect the peaks of each cuff pressure oscillation produced by the oscillometric technique, the result would be similar to a parabolic curve. The zenith of the parabolic curve would be the mean blood pressure value. Studies have shown that the systolic pressure value will be the cuff pressure at which the oscillations are about 0.75 of the oscillations occurring at mean pressure to the left or high pressure side of the curve, and the diastolic pressure value will be the cuff pressure at which the oscillations are about 0.8 of the oscillations occurring at mean pressure to the right or low pressure side of the curve. While the curve produced will be similar to a parabolic curve, the characteristics of the actual curve derived in each case will differ from subject to subject.

It is apparent that the aforesaid prior art oscillometric techniques will not produce the most accurate noninvasive pressure information because each pressure reading measured will be an actual cuff pressure, and these actual cuff pressures are created by stepped plateaus during deflation of the cuff. These prior art techniques will not identify pressure values which are true when they lie between the steps. Thus, there is a considerable built-in error factor inherent in these prior art procedures which utilize stepwise deflation of the cuff.

This invention is directed to an improved oscillometric procedure which utilizes a stepwise deflation of the cuff format but which obtains more accurate systolic, diastolic and mean blood pressure readings. The device includes a pressure cuff for affixation to the subject and a pump which automatically inflats the cuff to an initial pressure, which is calculated to be above the subject's systolic pressure. Operation of the pump, as well as the other components of the device, is controlled by an onboard computer. The pressure in the cuff is lowered stepwise, preferably in increments of 10% of previous pressure, and the cuff pressure oscillations are detected and stored as the dependent variable at each cuff pressure step during the deflating procedure. At the same time, the cuff pressures at each step are detected and stored as the independent variable by the computer. After the computer has detected that mean pressure has been passed, by reason of declining oscillations, the computer identifies the maximum oscillation which has been detected and programs the deflating mechanism to continue to deflate the cuff to a pressure which produces oscillations of about 0.6 the maximum oscillation measured. This will ensure that the cuff will be deflated past the diastolic pressure value. Once this level is reached, the cuff is emptied of air. The computer will then review the stored oscilations, identify the maximum value and its cuff pressure, and will also identify an oscillation value which occurred before maximum, and another oscillation value which occurred after maximum, as well as their respective cuff pressure values. Once the three oscillation values are determined, the computer fits the three oscillation values to a parabolic curve and calculates the peak oscillation value for that particular curve which has been fitted to the measured oscillations. The computer then uses the calculated parabolic equation to determine the cuff pressure at which this calculated peak oscillation would have occurred, this cuff pressure being the mean blood pressure value. This pressure is stored as the "true" mean blood pressure. It is submitted that this is as close as one can come to true mean blood pressure without invading the blood vessel.

In order to determine the "true" systolic pressure, the computer identifies the oscillation which is 0.75 of the calculated maximum oscillation, and then reviews the stored oscillations which occurred prior to the maximum measured oscillation. The computer identifies the two prior oscillations which straddle the calculated 0.75 maximum oscillation and notes the measured cuff pressures associated with each of the straddling oscillations. The computer then identifies the slope of the line connecting the two straddling oscillations and notes where, along that slope, the calculated 0.75 maximum oscillation would lie. Using the location of this point along the slope, the computer interpolates to determine what cuff pressure conforms to that point along the slope. The same procedure is followed to calculate "true" diastolic pressure using the 0.8 factor with the calculated maximum oscillation.

The device also measures pulse rate by measuring and storing the duration of each pause between the beginnings of successive oscillation rises. The beginning and ending data points are discarded and the measured actual pause durations are averaged. The actual measured pauses are then compared to the average, and any individual values which vary from the average by more than 10% are discarded. The remaining data is then re-averaged to calculate the accepted pulse rate.

The pulse rate, systolic, diastolic and mean pressures are all displayed, preferably on a digital readout.

Throughout the entire procedure of measuring the cuff pressure oscillation, any false or artifact oscillations which may occur from subject movement or bumping the cuff are ignored, and the pressure levels will be maintained until at least two actual arterial pressure oscillations have been detected. Detail of the artifact rejection means are set forth in greater detail hereinafter.

It is, therefore, an object of this invention to provide improved oscillometric blood pressure measuring device which automatically measures systolic, diastolic and mean blood pressure.

It is an additional object of this invention to provide a device of the character described wherein a true measurement of systolic, diastolic and mean blood pressure will be obtained.

It is a further object of this invention to provide a device of the character described which includes a microprocessor operable to fit a parabolic curve onto three measured cuff pressure values to determine the zenith of the curve and thereby the mean blood pressure value.

It is another object of this invention to provide a device of the character described wherein the true mean pressure is used to calculate true systolic and diastolic blood pressure values from adjacent measured cuff pressures.

These and other objects and advantages of the invention will become more readily apparent from the following detailed description of a preferred embodiment of the device taken in conjunction with the accompanying drawings, in which.

Figure 1:
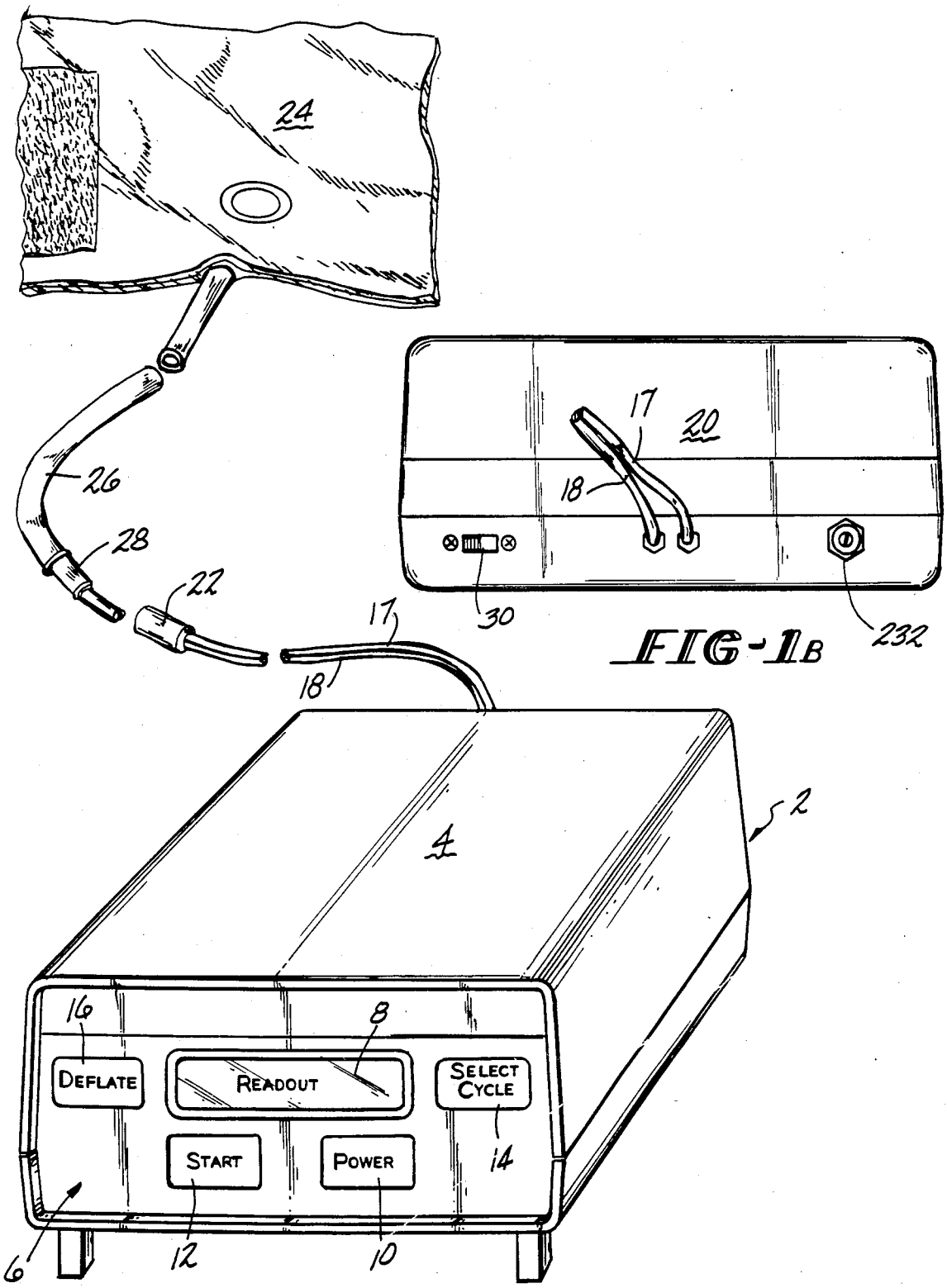
FIG. 1a is a perspective view of a preferred embodiment of a device formed in accordance with this invention.
FIG. 1b is a back elevational view of the casing of the device.

Referring now to the drawings, there is shown in FIG. 1 a preferred embodiment of the device of this invention designated generally by the numeral 2. The device 2 has a casing or housing 4 in which the mechanical and electrical components are contained. The device is powered by an onboard rechargeable battery disposed in the housing 4. The housing 4 has a front panel 6 which includes a readout area 8, a "power" on-off switch 10, a "start" switch 12, a "select cycle" switch 14, and a "deflate" switch 16. In the readout area, various messages will be displayed, as set forth hereinafter, and the blood pressure and pulse readings will also be displayed. The readout area uses a dot matrix or custom designed display. A number of preset messages will be displayed in the readout area relating to the device's operation and condition. When the device is first turned on by pressing the power switch, the message "SELF TEST IN PROGRESS" will be displayed as the device performs an internal systems check. If this check reveals an internal failure, the message "SELF TEST FAILED" will appear. This display will alternate every five seconds with the message "SERVICE REQUIRED." If the self check is positive, the message "INFLATE PRESS (---) CHANGE ON BACK" will appear. The bracketed portion refers to the initial pressure desired for the cuff. This can be either 200 mmHg or 150 mmHg, there being a switch on the back of the casing to make the selection. The next message to appear will be "MAN: PRESS START AUTO: PRESS CYCLE." This refers to the desired mode of operation of the device. If a single pressure reading is to be taken, then the "START" switch is pressed to inflate the cuff and begin the reading. If a repetitive cycle of readings is desired to monitor the subject, then the "SELECT CYCLE" switch is pressed. In the latter case, the message "SELECT TIME [ ] PRESS START" will appear. The numerals 1, 3, 5 or 10 will appear within the brackets and will refer to the time interval between testing cycles. Pressing the "SELECT CYCLE" switch will then change the number appearing within the brackets until the desired number appears. Thereafter, the "START" switch is pressed to begin the reading.

When the "START" switch is pressed, the message "MEASURING [ ] CUFF --- mmHg" will appear. The cycle selected will appear in the brackets, and the changing pressure in the cuff will be displayed before the "mmHg" display. As the cuff is stepwise deflated, the cuff pressure display will change accordingly. After the test is completed, the message "S:_____ M:_____ [ ] D:_____ P:_____ (---)" will appear with the measured systolic, mean and diastolic pressures measured being displayed where indicated. The pulse rate is also displayed. The pressures are displayed in mmHg units, and the pulse rate is displayed in beats per minute. When the cyclic mode is being used, the time interval until the next measurement will appear in brackets. When the manual mode is used, the data will be displayed for three minutes and then the device will turn itself off.

In addition to the aforesaid, certain other messages will appear in the readout area 8. When the battery has about one hour of operable life before requiring recharging, the message "LOW BATTERY" will be displayed after each test result is displayed. A beeping tone will also be emitted at 30 second intervals in such case. When the battery can power only one additional test, the message "BATTERY DEPLETED USE CHARGER" will appear. After this message, three audible beeps will occur and the device will shut itself off. In the event that it appears that the cuff has been improperly applied, or there is a kink or leak in the hoses, the message "LOOSE CUFF OR TUBE LEAK/KINK" will appear. In the event that the device does not sense two apparently valid arterial cuff oscillations, at any pressure level, then the message "EXCESSIVE MOTION REPEAT TEST" in manual, or "EXCESSIVE MOTION RETEST IN 2:00," in cyclic mode will appear. If a cuff pressure in excess of 300 mmHg is sensed, then the cuff will automatically deflate and the message "OVER PRESSURE REPEAT TEST" will appear. Should internal electronic circuitry malfunction occur, then the message "SYSTEM FAILURE SERVICE REQUIRED" will appear. This will be accompanied by 5 second interal beeps whereafter the device will shut down.

The front panel 6 also includes the "SELECT CYCLE" switch 14 and a "DEFLATE" switch 16. A pair of pneumatic hoses 17 and 18 extend through the back panel 20 to a female fitting 22. The cuff 24 (shown fragmentarily) is fitted to a pneumatic hose 26 terminating at a male fitting 28. Easy connect and disconnect between the device 2 and cuff 24 is thus realized.

Referring to FIG. 1b, the back panel 20 is shown. A reciprocating switch 30 is mounted thereon for selecting the desired full cuff pressure, either 150 mmHg or 200 mmHg. The battery charge socket 232 is located on the back panel 20 also. The battery is recharged by plugging the battery charger accessory into an outlet and plugging the charger cord jack into the socket 232.

Figure 2:
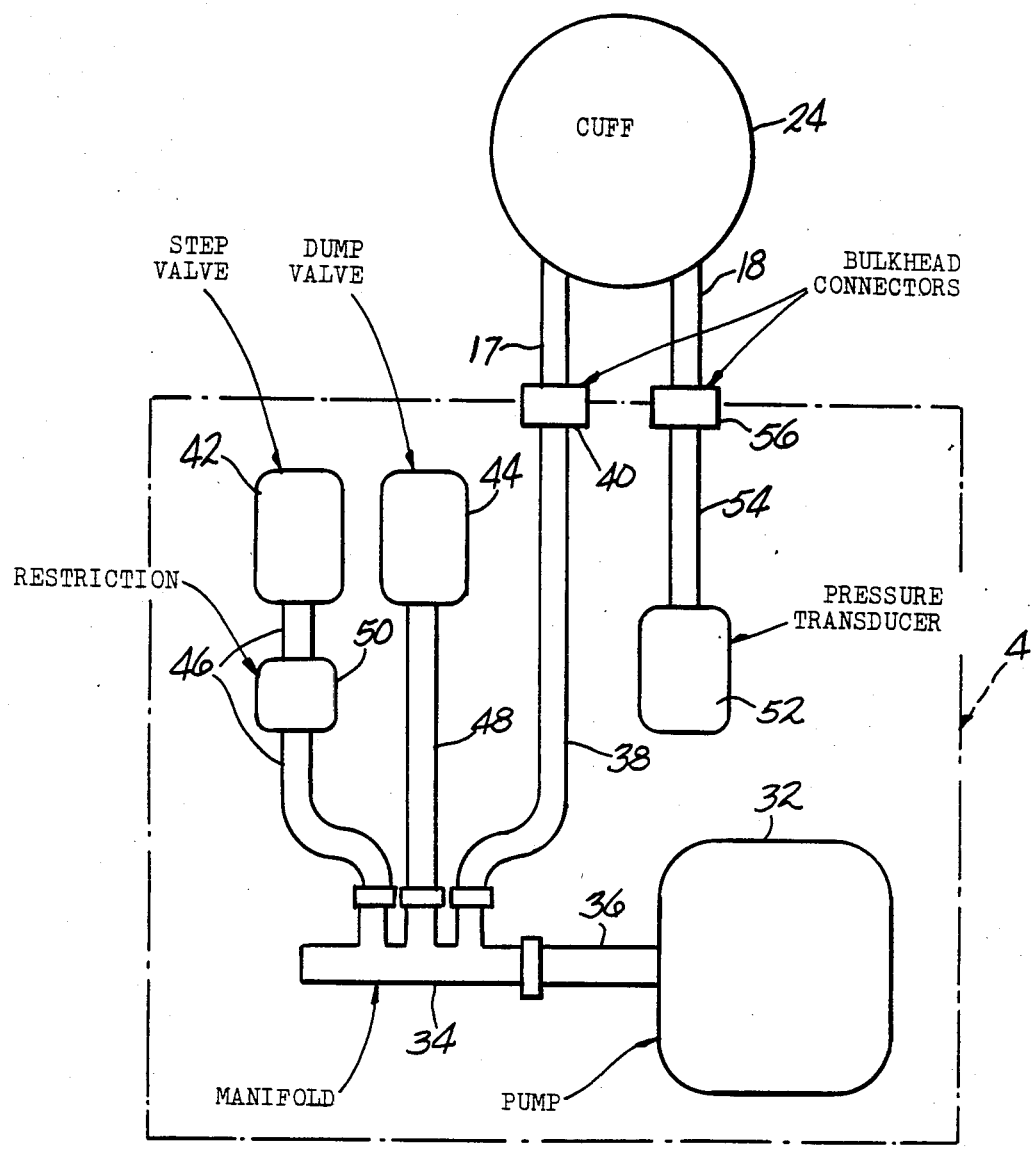
FIG. 2 is a somewhat schematic view of the mechanical components of the device.

Referring now to FIG. 2, there is shown, somewhat schematically, the mechanical pneumatic components of the device as they are arranged in the housing 4 (shown in phantom). As previously noted, the cuff 24 is connected to an inflation hose 17 and a cuff pressure/oscillation detector hose 18. An electrically operated pneumatic pump 32 is mounted in the housing 4 and is connected to a manifold 34 via a hose 36. The manifold 34 is connected via a hose 38 to a fitting 40 communicating with the inflation hose 17. A pair of venting valves 42 and 44 are connected to the manifold 34 by hoses 46 and 48 respectively. The valve 42 is a step valve which provides the controlled stepwise deflation of the cuff 24, and the valve 44 is dump valve which is used to empty the cuff 24 quickly in one bleed. Interposed between the manifold 34 and the step valve 42 is a restriction 50 comprising a small orifice which serves to slow the flow of air from the manifold 34 to the step valve 42. This element will be used in the embodiment of the device used to measure the blood pressure of infants. A pressure transducer 52 is connected to the pressure/oscillation detector hose 18 via a hose 54 and fitting 56. The transducer 52 monitors the pressure in the cuff 24 as well as oscillations in the cuff pressure caused by arterial pulses.

Figure 3:
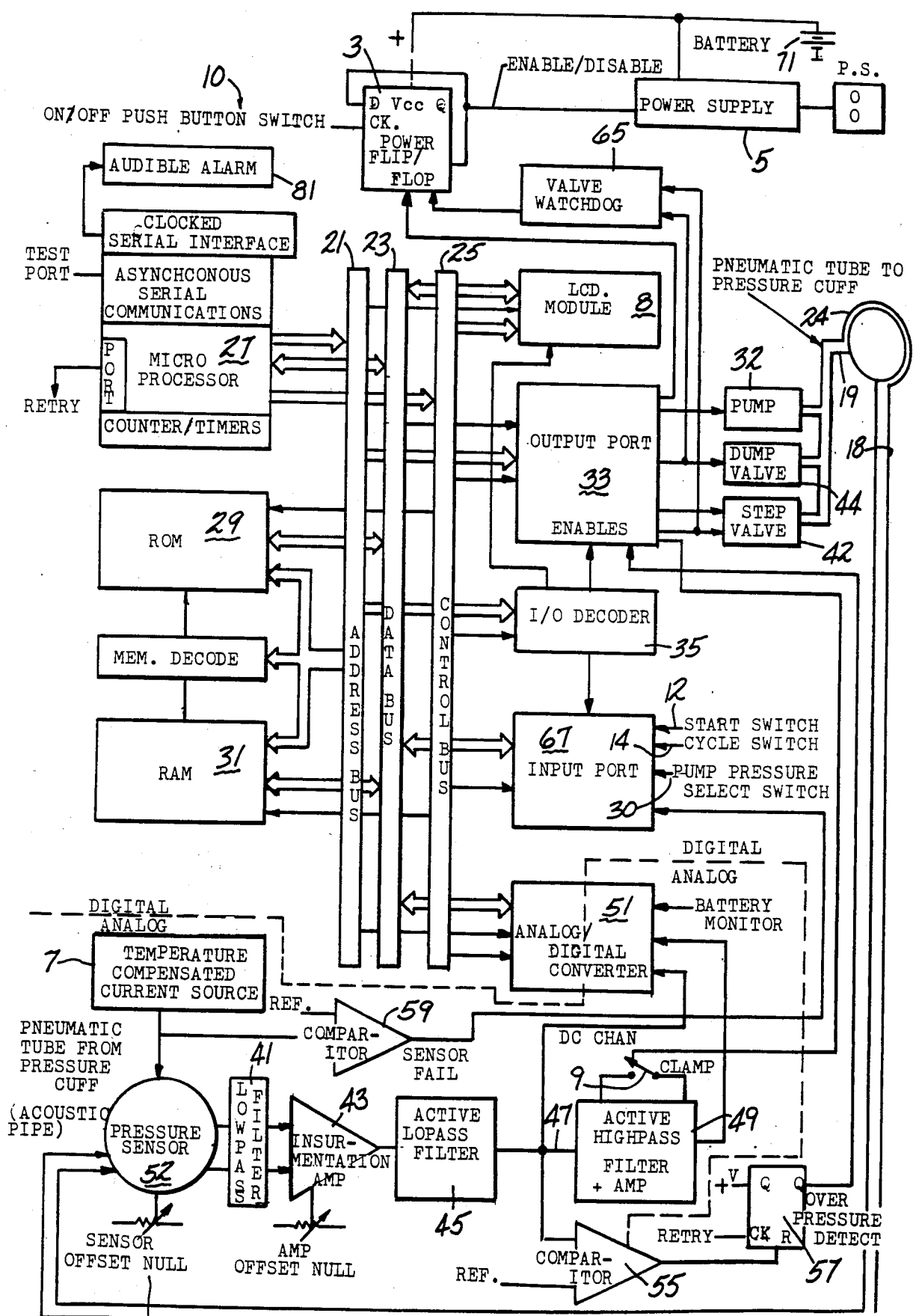
FIG. 3 is a circuit diagram of the electrical components of the device.

Referring now to FIG. 3, there is shown the electrical components and circuitry for the device.

The blood pressure monitor is of the type that operates under the control of a microprocessor. As such, the device utilizes a microprocessor for control, a programmable memory device to store the program or algorithm by which the unit operates, a random access memory device which acts as a location to store information during the operation of the monitor, and associated digital hardware. These devices communicate to each other on wires known as buses. Three distinct buses: an address bus, a data bus, and a control bus, allow the instrument to internally operate.

Button 10 is pushed to turn on the monitor. Flip-flop 3 is always powered by the battery 71 to allow it to watch for button 10 signals. Flip-flop 3 provides a high signal to turn on the power supply 5. After the power is on, the microprocessor 27 begins to control the monitor. The microprocessor points to its programmed memory (ROM) 29 via the address bus 21 to determine how to proceed. The controlling program in the ROM instructs the monitor to display prompt messages to the user on the LCD module 8. The user is asked to select an initial pump up pressure. The level may be changed by pushing the LEVEL select button 30. The program then queries the user to define the time intervals desired between tests. This cycle rate is changed by the CYCLE switch 14. Pressure measurement cycles by the monitor are initiated by START switch 12. All three of the above button pushes are sensed by the input port 67. Input port 67 feeds signals to the data bus 23. In this way the switches are able to communicate with the microprocessor.

A START signal causes the microprocessor to address the output port 33. The dump valve 44 and the step valve 42 are closed. The pump 32 is turned on causing air to flow through tube 38 into the cuff 24. The cuff is inflated while its internal pressure is monitored via tube 54 to a pressure transducer 52. The output voltage of the pressure transducer is sent through an electrical filter 41 to remove extraneous information. The voltage is then increased to a usable level by amplifier 43. The voltage is filtered again by filter 45 to allow only usable information that is within the physiological range. The resultant voltage at point 47 represents the absolute level of the cuff pressure including very small pressure pulses superimposed on the voltage. The voltage at 47 is sent to an analog-to-digital converter 51 that provides the microprocessor with information about the cuff pressure in digital form. The voltage 47 is also sent to a high pass filter and amplifier 49 which filters low frequencies, removes DC offset of cuff pressure, and amplifies the small pressure pulses that are contained within the signal. These pressure signals are sent to the analog-to-digital converter for processing by the microprocessor. The output from the amplifier 49 is restrained by clamping switch 9 during cuff deflation steps to minimize amplifier 49 settling time. The position of the switch 9 is controlled through the output port 33 by the microprocessor 27. Analog-to-digital converter information captured by the microprocessor is then operated upon by the stored program. The resultant calculations are displayed to the user on the LCD module.

The pressure transducer 52 requires a termperature independent electrical current source for maximum accuracy. This current is supplied by the temperature compensated current source 7. The zero pressure adjustment of the transducer output is made by a transducer offset adjustment potentiometer 39. Failure of the pressure transducer could result in harm to the patient, therefore, safety measures are taken to insure that the cuff cannot remain inflated without the control of the monitor. Comparator 59 compares the voltage across the pressure transducer 52 with a fixed reference voltage generated by the power supply 5. Failure of the transducer 52 will cause the comparator 59 to signal the microprocessor through the input port 67 that the transducer has failed. This will cause the monitor to terminate its testing and open the dump valve 44 and the step valve 42. An alarm condition will be displayed on the LCD module. A signal from comparator 55 will indicate that the voltage 47 is higher than that allowable for safe operation of the cuff on a patient. This will cause over-pressure detection circuit 57 to signal the microprocessor that an unsafe condition exists. The monitor will cease its testing and open all valves. A valve watchdog 65 insures that the valves are operating. When it detects no valve operations after a fixed period of time, it will reset flip-flop 3 removing power to the monitor. This will open the dump valve 44, removing pressure in the cuff. All alarm messages on the LCD module or abnormal operating conditions are emphasized by an audible alarm 81 which is controlled directly by the microprocessor through its clocked serial interface.

Figure 4:
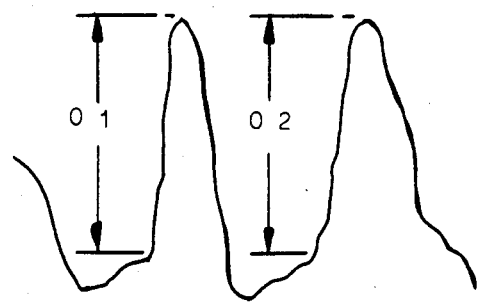
FIG. 4 is a representation of the wave form of normal arterial pulse oscillations imposed on the cuff.

Referring now to FIG. 4, there is shown a trace of a pair of normal arterial pulse oscillations as the computer "sees" them. The magnitude of these oscillations is what is being measured by the pressure transducer 52 and its associated filter/amplifier 41, 43. In FIG. 4, the characteristic measured is denoted by $O_1$, and $O_2$. When the computer sees two verified arterial pulse oscillations at the ongoing cuff pressure step, it will activate the step valve 42 to lower the cuff pressure to the next step, which is preferably about 10% lower. If, after maintaining the cuff pressure at a level for about 20 seconds, the computer has not seen two verified arterial pulse oscillations due to excessive subject motion, or the like, it will signal excessive motion and abort run.

Figure 5:
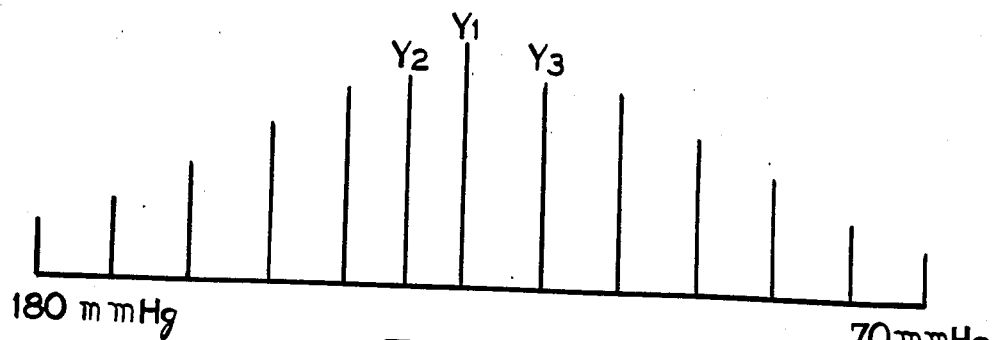
FIG. 5 is a representation of an oscillometric cycle showing the wave forms detected from above systolic pressure to below diastolic pressure.
Figure 6:
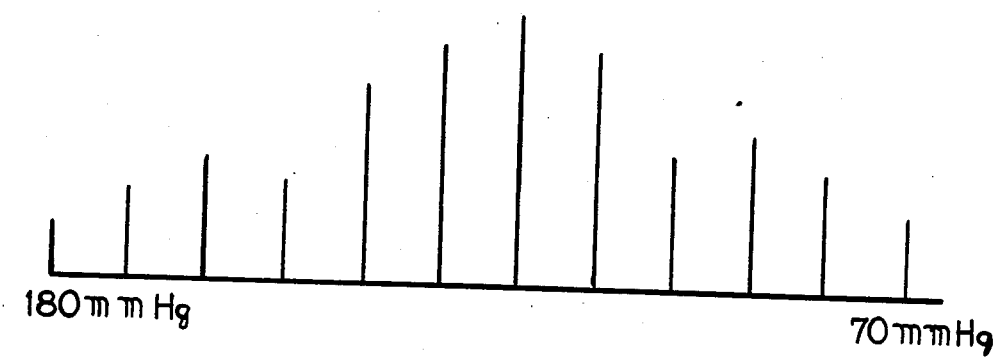
FIG. 6 is a representation of a similar oscillometric cycle but with several atypical oscillations included.
Figure 7:
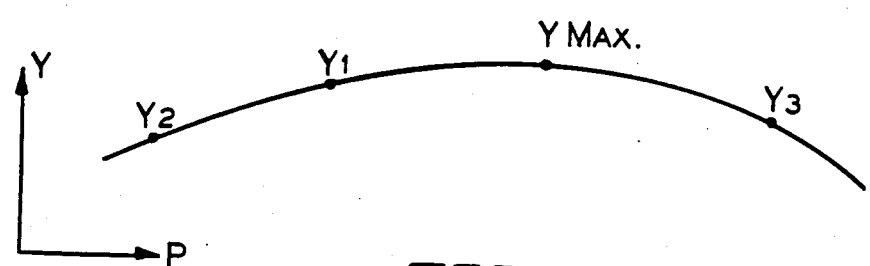
FIG. 7 is a representation of three of the wave form peaks as they are fitted with the parabolic curve, and showing the zenith of the curve which coincides with true mean blood pressure.

Referring to FIGS. 5 and 6, there are shown two representations of oscillation cycles which will be seen by the computer and stored in the RAM. It will be noted that the oscillations will increase from the initial systolic-plus cuff pressu to a maximum level whereupon the magnitude of the oscillations gradually decreases to the final diastolic-minus cuff pressure, after which air in the cuff is dumped. Along with each oscillation, the matching cuff pressure level will be stored in the RAM. When the cycle is finished, the computer reviews the stored data and identifies the highest magnitude oscillation noted; $Y_1$, and then identifies the next highest oscillations noted on either side of $Y_1$, which are denoted by $Y_2$ and $Y_3$. With these three points identified, the computer then fits a parabolic curve onto these three points and computes Y max on the curve, as noted in FIG. 7.

With each of the points $Y_1$, $Y_2$ and $Y_3$, both Y and P (cuff pressure) are known. Using three simultaneous equations f each point $Y_1$, $Y_2$ and $Y_3$, the parabolic equation $Y=AP^2+BP+C$ is solved for A, B and C for the particular curve fitted onto the points. Once A, B and C are calculated by the computer, the true mean pressure value can be calculated as $Pm=-0.5\ B/A$. Thereafter, Y max is calculated by solving the equation $Y\ max=AP_m^2+BP_m+C$.

Figure 8:
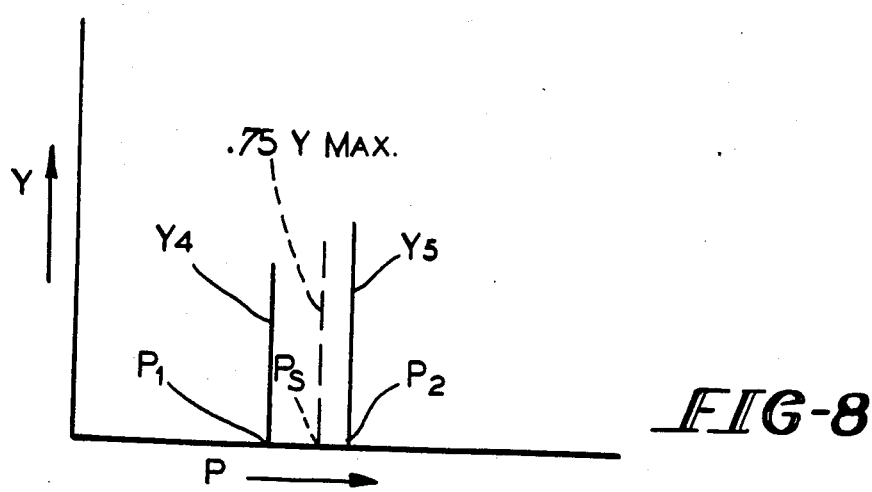
FIG. 8 is a representation of the manner in which true systolic blood pressure is calculated.

Referring to FIG. 8, after the true mean pressure Pm has been calculated, the computer takes the calculated Y max value and multiplies it by 0.75 to find the oscillation 0.75 Y max, which, on that curve, would have occurred at true systolic pressure. The two closest measured oscillations $Y_4$ and $Y_5$ on either side of that 0.75 Ymax systolic oscillation are identified and the measured cuff pressures $P_1$ and $P_2$ are noted which match those two closest measured oscillations. Using the proportions of the measured and calculated systolic oscillations, the computer interpolates between the two measured cuff pressures to calculate the true systolic cuff pressure $P_S$. The same procedure is followed to calculate true diastolic blood pressure using a factor of 0.8 of the calculated Y max.

Figure 9:
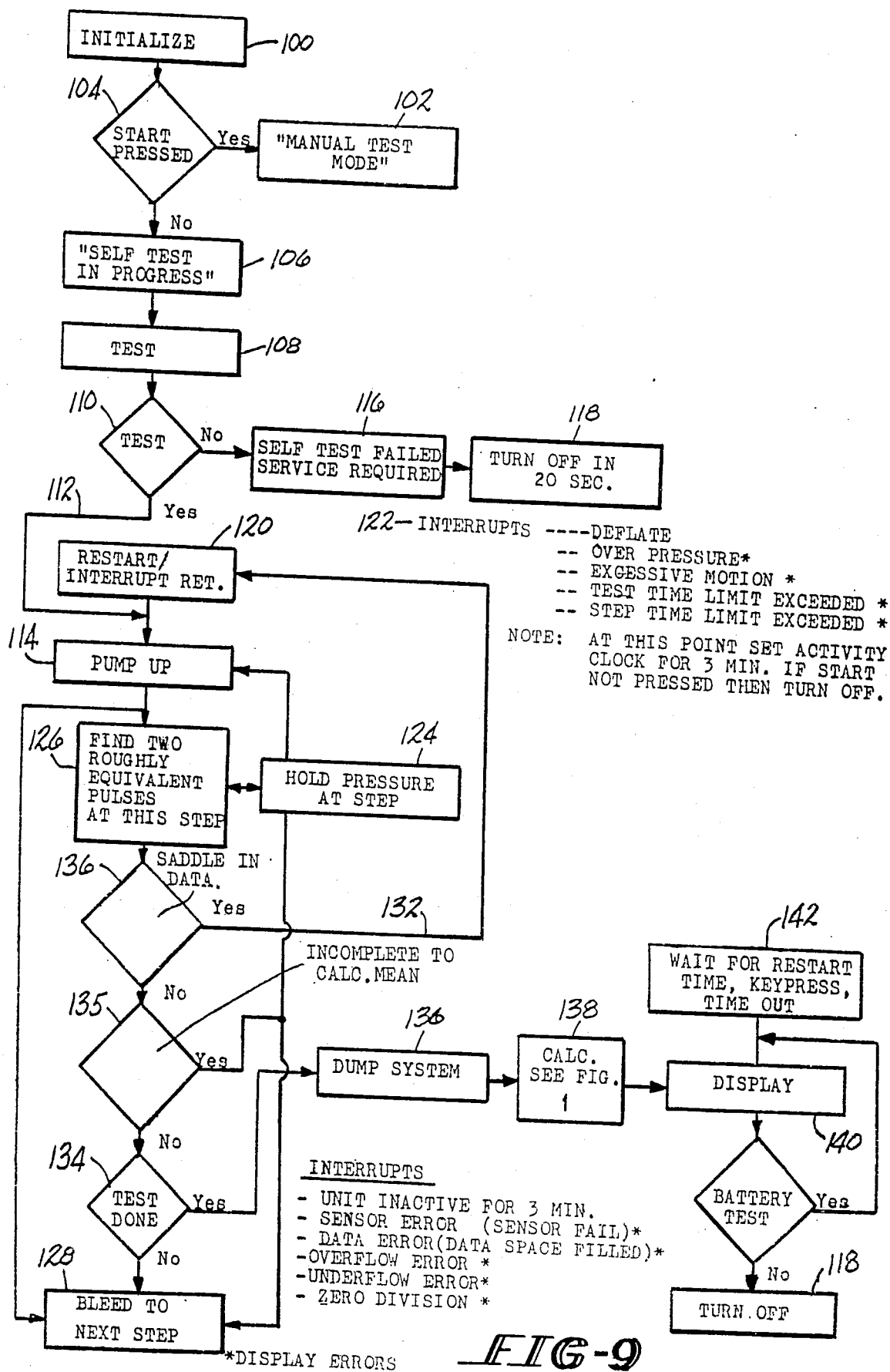
FIG. 9 is a flow chart of the software for operating a blood pressure testing cycle of the device.

Referring now to FIG. 9, there is shown a flow chart for the program used to obtain the oscillating data that the device uses. The oblong flag 100 denotes the "POWER" and "START" switches which, when actuated, initialize the device. The flag 102 denotes the "SELECT CYCLE" switch when set on "Manual Mode." When flag 104 is actuated, the device tests itself per flags 106 and 108. If the device tests out as operative, the microprocessor activates the pump per flag 110, line 112 and flag 114. If the device does not test out as operative, the flags 116 and 118 are activated by the computer. If the pump-up results in excessive cuff pressure, the flag 120 interrupts the pump-up whereupon flag 122 deflates the cuff and the pump-up is restarted. If there is no over pressure condition sensed, the flag 124 holds the pressure at the current step while the computer looks for two roughly equivalent oscillations at that step per flag 126. When such oscillations are noted, they, and the existent cuff pressure, are stored in the RAM whereupon the cuff is bled to the next pressure step per flag 128. In the event that such oscillations are not noted within 20 seconds, then the computer signals excessive motion and aborts run. The pressure-hold step is repeated per flag 124, and the search for the equivalent pulses is repeated per flag 126. The computer monitors the oscillations noted and if it notes any saddles caused by artifact oscillations which do not fit the other oscillation peaks, such as shown in FIG. 6 at $Y_A$, then flag 136 interrupts the test and returns control to flag 120 via line 132. If no saddles or incomplete data (per flag 135) are noted, then the testing continues until the cuff pressure is below diastolic, whereupon flag 134 is satisfied so that the cuff pressure is dumped per flag 136. The computer then performs the calculations per flag 138 as shown in the flow charts of FIGS. 10-12. When the calculations are completed, the values are displayed per flag 140, whereupon the device waits for its next run per flag 142.

Figure 10:
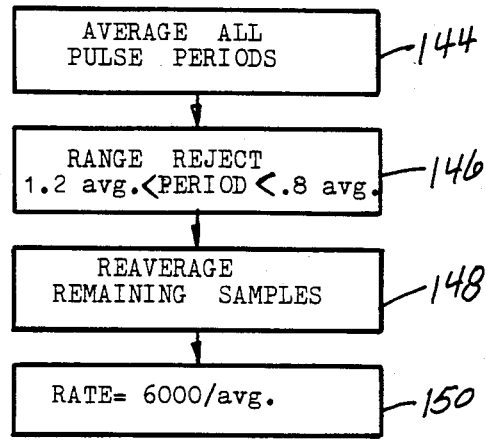
FIG. 10 is a flow chart for the calculation of pulse rate program.
Figure 11:
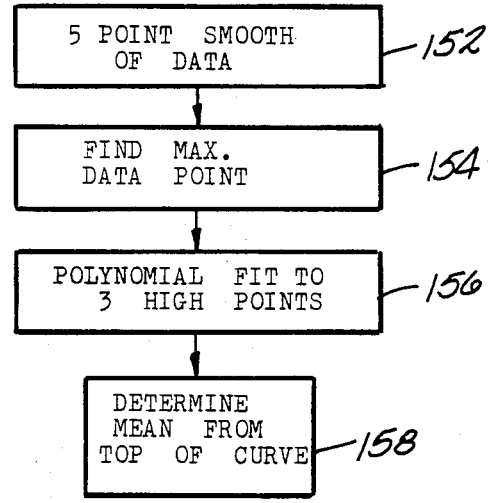
FIG. 11 is a flow chart for the calculation of mean arterial pressure program.
Figure 12:
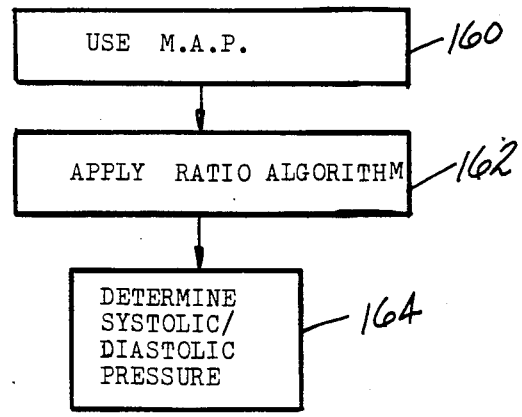
FIG. 12 is a flow chart for the calculation of the systolic and diastolic pressures program.

FIG. 10 shows the steps 144, 146, 148 and 150 for calculating the pulse rate. FIG. 11 shows the steps 152, 154, 156 and 158 for determining the mean arterial pressure, and FIG. 12 shows the steps 160, 162 and 164 for determining the systolic and diastolic pressures from the mean arterial pressure (M.A.P.)

It will be readily appreciated that the device of this invention will provide the most accurate measurement of mean blood pressure possible without invading an artery. Additionally, statistically accurate diastolic and systolic measurements are provided, along with pulse rate determination. The device has many safety features, the capability of analyzing its data for artifacts, and rejecting artifact-impaired tests. The device, moreover, is lightweight, compact and of simple inexpensive manufacture.

Since many changes and variations of the disclosed embodiment of the invention may be made without departing from the inventive concept, it is not intended to limit the invention otherwise than as required by the appended claims.

What is claimed is:

1. A device for automatic determination of blood pressure values using a non-invasive oscillometric technique, said device comprising:
   (a) a cuff means for girdling securement to a subject whose pressure is to be measured;

(b) pump means operably connected to said cuff means for inflating said cuff means to an initial pressure;

(c) valve means operably connected to said cuff means for venting air from aid cuff means to lower the pressure thereof;

(d) sensor means operably connected to said cuff means for sensing cuff pressure and oscillations in cuff pressure caused by arterial pulsations of the subject;

(e) memory means for storing cuff pressure data and cuff pressure oscillation data obtained from said sensor means; and (f) computer means operably connected to said valve means, to said sensor means, and to said memory means, said computer means being operable to:

(i) actuate said valve means to periodically cause deflation of said cuff means in serial steps until a predetermined terminal cuff pressure step is reached;

(ii) record cuff pressure measurements at each pressure step;

(iii) record arterial cuff pressure oscillations at each pressure step;

(iv) collate each of said recorded cuff pressure measurements with the respective arterial cuff pressure oscillations and store said collated pressure measurements and pressure oscillations in said memory means;

(v) after said terminal cuff pressure step is reached, identify three stored arterial oscillation values, which include at least the greatest cuff pressure oscillation value and the next greatest oscillation values on each side of said greatest oscillation value, and their collated cuff pressure measurements;

(vi) fit a curve to said three oscillation values; and (vii) calculate true means blood pressure from said curve.

2. The device of claim 1, wherein said curve is a parabolic curve produced by solving the equation $$Y = Ap^2 + Bp + C$$

where A, B and C are constants, Y is the oscillation value and p is the cuff pressure measurement, said equation being solved wit simultaneous equations using the three stored oscillation values and their collated cuff pressure measurements.

3. The device of claim 2 wherein said true mean blood pressure is calculated by solving the equation $Pm = -0.5 \, B/A$ wherein Pm is the true mean blood pressure.

4. The device of claim 1 wherein said computer means is operable to fully deflate said cuff means when detected cuff pressure oscillations occurring subsequent to the maximum cuff pressure oscillations measured are equal to approximately 0.6 of the maximum cuff pressure oscillations measured.

5. The device of claim 1 wherein said computer means is operable to calculate systolic pressure as a function of the maximum oscillation described by said parabolic curve.

6. The device of claim 1 wherein said computer means is operable to calculate diastolic pressure as a function of the maximum oscillation described by said parabolic curve.

7. The device of claim 1 further comprising means forming an air flow restriction between said cuff means and said valve measn for controllling the rate of venting of said cuff means to adapt the device for neonatal use.

8. A device for use in combination with a cuff for automatic determination of blood pressure values using a non-invasive oscillometric technique, said device comprising:

(a) a pump for inflating the cuff;

(b) a first valve for venting air stepwise from the cuff to lower pressure in the cuff to successively lower pressure plateaus;

(c) sensor means for sensing cuff pressure at each pressure plateau, and for sensing oscillations in cuff pressure caused by arterial pulsations at each pressure plateau;

(d) means for storing collated cuff pressure data and cuff pressure oscillation data obtained from said sensor means. said cuff pressure oscillation data including at least the greatest cuff pressure oscillation value, and the next greatest oscillation values on each side of said greatest oscillation value; and (e) computer means operable to fit a parabolic curve onto said cuff pressure oscillation data and to calculate true mean blood pressure from said parabolic curve and the stored cuff pressure data.

9. The device of claim 8 wherein said computer means determines said parabolic curve by solving the equation:

$$Y = AP^2 + BP + C$$

wherein Y is cuff pressure oscillation, P is the collated cuff pressure, and A, B and C are constants, said equation being solved for A, B and C with simultaneous equations using three stored cuff pressure oscillation measurements and their collated cuff pressure measurements.

10. The device of claim 9 wherein said computer means calculates true mean pressure by solving the equation:

$$Pm = -0.5 \, B/A$$

wherein Pm is true mean pressure.

11. The device of claim 10 further comprising display means operably connected to said computer means for displaying the calculated true mean pressure.

12. The device of claim 11 wherein said computer means calculates systolic and diastolic pressure from said parabolic curve as cuff pressure values corresponding to oscillation values on said parabolic curve occurring at an ascending oscillation equal to approximately 0.75 of the maximum oscillation which correlates with Pm and a descending oscillation equal to approximately 0.8 of said maximum oscillation.

13. A method of measuring blood pressure values, said method comprising the steps of:

(a) encircling a limb of a subject with an inflatable pressure cuff;

(b) inflating said pressure cuff to an initial pressure;

(c) incrementally deflating said pressure cuff through a series of desending pressure plateaus;

(d) maintaining constant pressure at each of said pressure plateaus while measuring and recording cuff pressure values and cuff pressure oscillation values at each pressure plateau;

(e) storing said measured cuff pressure values and cuff pressure oscillation values in collated fashion;

(f) repeating steps (c) (d) and (e) until a preset terminal cuff pressure plateau is reached;

(g) fitting a parabolic curve to stored oscillation values which include at least the greatest cuff pressure oscillation value and the next greatest oscillation values on each side of said greatest oscillation value; and (h) calculating true mean pressure from said parabolic curve.

14. The method of claim 13 further comprising the steps of completely deflating said cuff when measured cuff pressure oscillation values occurring subsequent to a measured maximum cuff pressure oscillation value are less than or equal to about 0.6 of said measured maximum cuff pressure oscillation value.

15. The method of claim 13 wherein said parabolic curve is fitted onto a set of measured cuff pressure oscillations comprising the three greatest oscillations measured.

16. The method of claim 15 wherein the parabolic curve is derived from identifying constants A, B and C by solving equations:

$$Y_1 = AP_1^2 + BP_1 + C;$$

$$Y_2 = AP_2^2 + BP_2 + C; \text{ and}$$

$$Y_3 = AP_3^2 + BP_3 + C$$

wherein $Y_1$ equals the maximum measured cuff pressure oscillation and $P_1$ equals its collated measured cuff pressure; $Y_2$ equals the greatest measured cuff pressure oscillation occurring prior to $Y_1$ and $P_2$ equals its collated measured cuff pressure; and $Y_3$ equals the greatest measured cuff pressure oscillation occurring subsequent to $Y_1$ and $P_3$ equals its collated measured cuff pressure.

17. The method of claim 16 wherein true mean blood pressure is derived from the equation:

$$P_m = -0.5 \, B/A$$

where $P_m$ equals true mean blood pressure.

* * * * *